United States Patent
Papania-Davis et al.

(10) Patent No.: US 12,025,609 B2
(45) Date of Patent: *Jul. 2, 2024

(54) METHOD TO PRODUCE EVOLVING CONCRETE MIXTURE HEURISTIC

(71) Applicant: X Development LLC, Mountain View, CA (US)

(72) Inventors: Antonio Raymond Papania-Davis, Oakland, CA (US); Weishi Yan, Oakland, CA (US)

(73) Assignee: X Development LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/329,298

(22) Filed: Jun. 5, 2023

(65) Prior Publication Data

US 2023/0314404 A1   Oct. 5, 2023

Related U.S. Application Data

(63) Continuation of application No. 17/671,109, filed on Feb. 14, 2022, now Pat. No. 11,703,499.

(Continued)

(51) Int. Cl.
*G01N 33/38* (2006.01)
*G01N 11/00* (2006.01)
(Continued)

(52) U.S. Cl.
CPC ........... *G01N 33/383* (2013.01); *G01N 11/00* (2013.01); *G01N 15/14* (2013.01); *G06F 30/25* (2020.01);
(Continued)

(58) Field of Classification Search
CPC ...... G01N 33/383; G01N 11/00; G01N 15/14; G01N 2015/1493; G01N 2015/1497;
(Continued)

(56) References Cited

U.S. PATENT DOCUMENTS

| | | | |
|---|---|---|---|
| 5,527,387 A | 6/1996 | Andersen et al. | |
| 5,943,234 A | 8/1999 | Martinez et al. | |

(Continued)

FOREIGN PATENT DOCUMENTS

| | | |
|---|---|---|
| CN | 104926219 | 9/2015 |
| CN | 104926219 A * | 9/2015 |

(Continued)

OTHER PUBLICATIONS

Amberger et al., "Approximation of Objects by Spheres for Multisphere Simulations in DEM," European Congress on Computational Methods in Applied Sciences and Engineering (ECCOMAS 2012), Sep. 10-14, 2012, 14 pages.

(Continued)

*Primary Examiner* — Michelle M Iacoletti
(74) *Attorney, Agent, or Firm* — Fish & Richardson P.C.

(57) ABSTRACT

Methods, systems, and apparatus for generating a recipe for a concrete mixture, comprising: obtaining an optical characterization of a set of particles; determining, based on the optical characterization, physical characteristics of the set of particles; generating a multispherical approximation of the set of particles; selecting, based on the physical characteristics of the set of particles and from a database of performance rules, performance rules applicable to the set of particles; predicting performance of a proposed recipe for a concrete mixture formed from the set of particles by: determining a wet flowability rating of the proposed recipe based on the selected performance rules; and determining a dry packing rating of the proposed recipe based on the multispherical approximation; iteratively altering the proposed recipe and predicting performance of the altered proposed recipe until the predicted performance satisfies performance criteria to obtain a final recipe; and outputting the final recipe.

20 Claims, 7 Drawing Sheets

Related U.S. Application Data

(60) Provisional application No. 63/248,365, filed on Sep. 24, 2021.

(51) Int. Cl.
| | |
|---|---|
| *G01N 15/14* | (2024.01) |
| *G06F 30/25* | (2020.01) |
| *G06F 113/02* | (2020.01) |
| *G06F 113/26* | (2020.01) |
| *G06F 119/02* | (2020.01) |
| *G16C 60/00* | (2019.01) |

(52) U.S. Cl.
CPC ..... *G16C 60/00* (2019.02); *G01N 2015/1493* (2013.01); *G01N 2015/1497* (2013.01); *G06F 2113/02* (2020.01); *G06F 2113/26* (2020.01); *G06F 2119/02* (2020.01)

(58) Field of Classification Search
CPC ..... G16C 60/00; G06F 30/25; G06F 2113/26; G06F 2119/02; G06F 2113/02
See application file for complete search history.

(56) References Cited

U.S. PATENT DOCUMENTS

| | | | |
|---|---|---|---|
| 7,104,142 B2 | 9/2006 | Martinez et al. | |
| 7,308,339 B2* | 12/2007 | Bonissone | G05B 13/0275 |
| | | | 700/265 |
| 7,386,368 B2* | 6/2008 | Andersen | G06F 30/20 |
| | | | 700/265 |
| 9,533,429 B2 | 1/2017 | Phares et al. | |
| 9,738,562 B2 | 8/2017 | Monkman et al. | |
| 9,766,221 B2 | 9/2017 | Radjy | |
| 9,789,629 B2 | 10/2017 | Koehler et al. | |
| 10,768,130 B2 | 9/2020 | Ghods et al. | |
| 10,865,143 B2 | 12/2020 | Ali et al. | |
| 11,332,655 B2* | 5/2022 | Morgan | C09K 8/42 |
| 2008/0009976 A1 | 1/2008 | Andersen et al. | |
| 2008/0115696 A1 | 5/2008 | Compton et al. | |
| 2009/0158969 A1 | 6/2009 | Andersen et al. | |
| 2009/0239970 A1* | 9/2009 | Rodrigues | A61L 24/06 |
| | | | 523/117 |
| 2011/0004333 A1 | 1/2011 | Andersen | |
| 2014/0249788 A1* | 9/2014 | Marchand | G06F 30/20 |
| | | | 703/6 |
| 2015/0142336 A1* | 5/2015 | Sant | G01N 33/383 |
| | | | 702/30 |
| 2015/0225295 A1 | 8/2015 | McCandlish et al. | |
| 2016/0223512 A1* | 8/2016 | Radjy | G01N 25/20 |
| 2018/0045621 A1* | 2/2018 | Radjy | G01N 33/383 |
| 2021/0035036 A1 | 2/2021 | Tregger et al. | |
| 2021/0209564 A1 | 7/2021 | Di Maio et al. | |
| 2021/0253480 A1 | 8/2021 | Mahoutian | |
| 2021/0371342 A1 | 12/2021 | Salami et al. | |
| 2022/0013196 A1 | 1/2022 | Monkman et al. | |
| 2022/0194852 A1 | 6/2022 | Thomas et al. | |
| 2022/0234249 A1 | 7/2022 | Papania-Davis et al. | |
| 2022/0235258 A1 | 7/2022 | Morgan et al. | |
| 2023/0093848 A1 | 3/2023 | Nagatani | |
| 2023/0100229 A1 | 3/2023 | Bush et al. | |

FOREIGN PATENT DOCUMENTS

| | | | | |
|---|---|---|---|---|
| CN | 113392570 | | 9/2021 | |
| CN | 113392570 A | * | 9/2021 | |
| EP | 2026226 | | 12/2009 | |
| GB | 2597404 | | 1/2022 | |
| IN | 202241041685 | | 7/2022 | |
| RU | 2728755 C1 | | 7/2020 | |
| WO | WO 95/05350 | | 2/1995 | |
| WO | WO 2013/185019 | | 12/2013 | |
| WO | WO 2020/204954 | | 10/2020 | |
| WO | WO-2020204954 A1 | * | 10/2020 | ............ C04B 28/02 |
| WO | WO 2022/164654 | | 8/2022 | |

OTHER PUBLICATIONS

Cheng-Qing et al., "Multi-sphere approximation of real. particl.es for DEM simulation based on a modified greedy heuristic algorithm," Powder Technology, Dec. 1, 2015, 286:478-487.

Cook et al., "Investigation of Optimize Graded Concrete for Oklahoma—Phase 1," Final Report—FHWA-OK-13-12, ODOT SP&R Item No. 2160, Oklahoma Department of Transportation, Oct. 2013, 118 pages.

Cook et al., "Investigation of Optimized Graded Concrete for Oklahoma—Phase 2," Final Report ~ FHWA-OK-15-07, ODOT SP&R Item No. 2253, Oklahoma Department of Transportation, Oct. 2015, 156 pages.

Cui et al., "DEM simulation of scc flow in L-Box set-up: Influence of coarse aggregate shape on scc flowability," Cement and Concrete Composites, Feb. 11, 2020, 109:103558.

DeRousseau et al., "Computational Design Optimization of Concrete Mixtures: A Review," Cement and Concrete Research, 2018, 35 pages.

International Search Report and Written Opinion in International Appln. No. PCT/US2022/043483, dated Dec. 22, 2022, 15 pages.

International Search Report and Written Opinion in International Appln. No. PCT/US2022/044257, dated Jan. 23, 2023, 17 pages.

Li et al., "Multi-sphere approximation of real particles for DEM simulation based on a modified greedy heuristic algorithm," Powder Technology, Dec. 1, 2015, 286:478-487.

Popescu et al. (3D reconstruction of existing concrete bridges using optical methods, Structure and Infrastructure Engineering 2019, vol. 15, No. 7, 912-924) (Year: 2019).

* cited by examiner

METHOD TO PRODUCE EVOLVING CONCRETE MIXTURE HEURISTIC

CROSS-REFERENCE TO RELATED APPLICATIONS

This application is a continuation of U.S. application Ser. No. 17/671,109, filed Feb. 14, 2022, which claims the benefit of U.S. Provisional Application No. 63/248,365, filed Sep. 24, 2021, the contents of which are incorporated by reference herein.

BACKGROUND

Concrete is the second most consumed substance (by mass) on our planet and is responsible for seven to eight percent of global carbon dioxide emissions. Concrete's material properties are inconsistent due to the large variation in ingredient material (e.g., aggregates) and processing. This material inconsistency requires large safety margins for a given performance level and results in material overuse. Advances in concrete preparation that can optimize the use of locally available materials to maximize concrete performance while minimizing cost with both traditional and non-traditional concrete ingredients are desirable.

SUMMARY

In general, this disclosure relates to a process and system for generating recipes for concrete mixes that can be tailored to availability of materials in different geological regions. The recipes can be adjusted based on characteristics of aggregate particles such as size, shape, and surface texture. The disclosed techniques can be used to efficiently simulate characteristics of particles in order to predict performance of a mixture of particles in both a fluid state and a cured, static state.

In general, concrete ingredients are characterized as they are measured for addition to a concrete mixture. The characterizations can be evaluated using empirical rules and physics simulators to predict both wet flowability and dry packing performance of a mixture formed from a combination of the ingredients. Based on the predicted performance, a recipe for the concrete mixture can be selected and a concrete mixture can be mixed using the selected recipe. Performance tests can then be performed on the concrete mixture. The empirical rules can then be updated based on results of the performance tests.

In some examples, ingredients are characterized by a particle analyzer that employs various sensors to detect characteristics such as particle size, particle shape, particle volume, and/or particle surface area. A dimensional reduction system can perform extraction of lower dimensional physical characteristics of particles.

Based on the extracted lower dimensional characteristics, empirical rules can be selected from a rules database. The empirical rules can include, for example, tarantula curves and coarseness factor charts. A performance evaluator can use the selected empirical rules to determine whether a proposed concrete recipe will satisfy wet flowability performance requirements. The performance evaluator can output a wet flowability rating to an optimizer, such as a Bayesian optimizer.

The extracted lower dimensional characteristics can also be used to generate a multisphere approximation model. Parameters for multisphere generation will be learned by machine learning models such as an encoder/decoder network, and then the parameters are fed into a generation algorithm. A physics simulator such as a discrete element method (DEM) model can use the approximated multispherical models to determine whether the proposed concrete recipe will satisfy dry packing performance requirements. The physics simulator can output a dry packing rating to the optimizer.

The optimizer can determine, based on the wet flowability rating and the dry packing rating, whether the proposed concrete recipe is likely to satisfy performance criteria. In some examples, based on determining that the proposed recipe will not likely satisfy performance criteria, the optimizer proposed a new proposed concrete recipe. In some examples, based on determining that the proposed recipe will likely satisfy performance criteria, the optimizer outputs a final concrete recipe.

The final concrete recipe can be used to create a concrete mixture. Empirical tests can be performed on the concrete mixture. Based on the empirical tests, the empirical rules can be updated in the rules database. In this way, the empirical rules in the rules database can be tuned for the various aggregate particle characteristics, improving accuracy of the performance simulations.

In general, innovative aspects of the subject matter described in this specification can be embodied in a method of generating a recipe for a concrete mixture, including: obtaining an optical characterization of a set of particles; determining, based on the optical characterization, physical characteristics of the set of particles; generating, by applying the physical characteristics of the set of particles to an autoencoder, a multispherical approximation of the set of particles; selecting, based on the physical characteristics of the set of particles and from a database of performance rules, performance rules applicable to the set of particles to obtain selected performance rules; predicting performance of a proposed recipe for a concrete mixture formed from the set of particles to obtain a predicted performance by: determining a wet flowability rating of the proposed recipe based on the selected performance rules; and determining a dry packing rating of the proposed recipe based on the multispherical approximation; iteratively altering the proposed recipe and predicting performance of the altered proposed recipe until the predicted performance satisfies performance criteria to obtain a final recipe; and outputting the final recipe.

In general, innovative aspects of the subject matter described in this specification can be embodied in a method of generating a recipe for a concrete mixture, including: obtaining an optical characterization of a set of particles; determining, based on the optical characterization, physical characteristics of the set of particles; selecting, from a database of multispherical approximations and based on the physical characteristics, a multispherical approximation of the set of particles; selecting, based on the physical characteristics of the set of particles and from a database of performance rules, performance rules applicable to the set of particles to obtain selected performance rules; predicting performance of a proposed recipe for a concrete mixture formed from the set of particles to obtain a predicted performance by: determining a wet flowability rating of the proposed recipe based on the selected performance rules; and determining a dry packing rating of the proposed recipe based on the multispherical approximation; iteratively altering the proposed recipe and predicting performance of the altered proposed recipe until the predicted performance satisfies performance criteria to obtain a final recipe; and outputting the final recipe.

These and other embodiments may each optionally include one or more of the following features, alone or in combination. In some implementations, the method includes mixing a concrete mixture using the final recipe; evaluating performance of the concrete mixture using one or more performance tests; and updating the performance rules based on the evaluated performance of the concrete mixture.

In some implementations, updating the performance rules includes generating, based on the evaluated performance, a limit curve for sets of particles matching the physical characteristics of the set of particles.

In some implementations, updating the performance rules includes adjusting, based on the evaluated performance, a limit curve of the database of performance rules for sets of particles matching the physical characteristics of the set of particles.

In some implementations, the performance rules include curves representing wet flowability limits.

In some implementations, iteratively altering the proposed recipe and predicting performance of the altered proposed recipe includes: obtaining data representing ingredients of the multispherical approximation; and altering a first proposed recipe to generate a second proposed recipe based on the wet flowability rating of the first proposed recipe, the dry packing rating of the first proposed recipe, and the data representing the ingredients of the multispherical approximation.

In some implementations, the method includes determining the dry packing rating by applying the multispherical approximation of the set of particles to a physics simulator.

In some implementations, the physics simulator includes a discrete element method simulator.

In some implementations, the performance criteria includes a highest dry packing rating subject to an acceptable wet flowability rating.

In some implementations, obtaining the optical characterization of the set of particles includes scanning the set of particles with an imaging device.

In some implementations, the physical characteristics of the particles include one or more of particle size, particle shape, or particle sphericity.

In some implementations, the multispherical approximation has reduced dimensionality compared to the optical characterization.

In some implementations, the physical characteristics have reduced dimensionality compared to the optical characterization.

In some implementations, the optical characterization of the set of particles includes heightmap representations of the set of particles.

In some implementations, determining the physical characteristics of the set of particles includes applying the heightmap representations of the particles to a dimension reducer to obtain the physical characteristics of the particles.

In some implementations, the optical characterization of the set of particles includes three-dimensional representations of the set of particles.

In some implementations, determining the physical characteristics of the set of particles includes applying the three-dimensional representations of the particles to a dimension reducer to obtain the physical characteristics of the particles.

Other embodiments include corresponding computer systems, apparatus, computer program products, and computer programs recorded on one or more computer storage devices, each configured to perform the actions of the methods. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
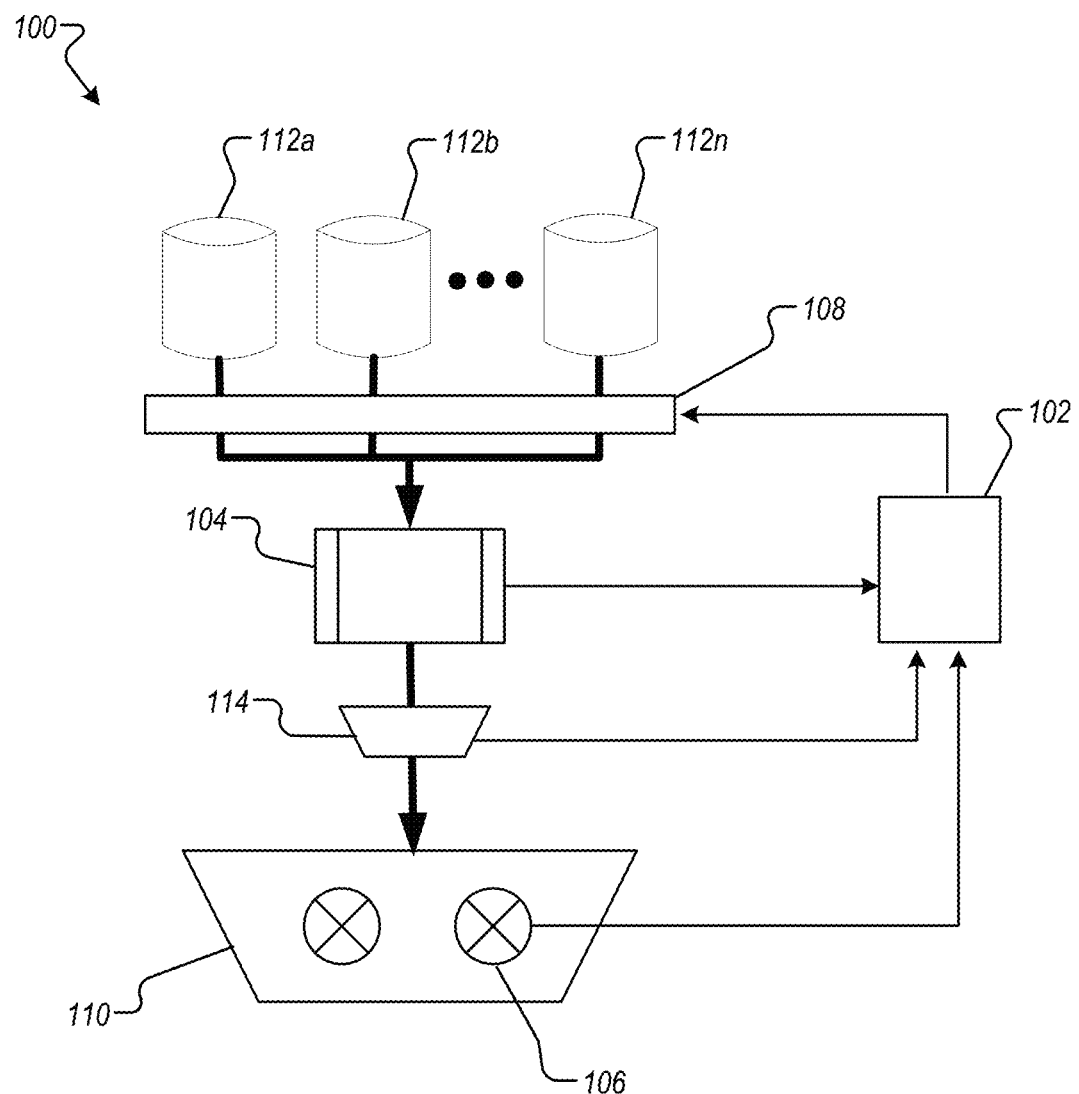
FIG. 1 depicts an exemplary concrete preparation system.

FIG. 1 depicts an exemplary concrete preparation system 100. In operation, concrete preparation system 100 measures characteristics of the raw ingredients of a concrete mixture. Concrete preparation system 100 can adaptively adjust the proportion of the raw ingredients added to the concrete mixture based on the measured characteristics to more accurately achieve desired structural properties in the final cured concrete. The operation of the system 100 is described in more detail below in reference to FIGS. 2 to 5.

Concrete preparation system 100 includes a control system 102. The control system 102 receives input from particle analyzing system 104 and concrete mix sensors 106. The control system 102 can control the operations of one or more ingredient metering systems 108 based on analyses of data obtained from one or both of the particle analyzing system 104 and concrete mix sensors 106, and based on modeling and simulation of aggregate mixes.

Concrete preparation system 100 includes raw ingredient storage bays or hoppers 112a-112n. The ingredient metering system 108 conveys the raw ingredients from the storage bays 112a-112n to a mixing vessel 110. For example, the ingredient metering system 108 can include a series of conveyors and augers to transfer raw ingredients from the storage bays 112a-112n into the mixing vessel 110. The concrete preparation system 100 differs from traditional concrete plants in that the raw ingredients are passed through the particle analyzing system 104 prior to delivery to the mixing vessel 110.

In some implementations, the ingredient metering system 108 may include a metering hopper 114 between the particle analyzing system 104 and the mixing vessel 110. The metering hopper 114 may be used to collect and measure (e.g., weigh) a raw ingredient as it passes through the particle analyzing system 104. For example, the weight of the ingredient measured by metering hopper 114 can be passed to the control system 100 permitting the control system to monitor the weight of the ingredient being measured in real-time. The control system 102 may then be able to make in-situ adjustments to how much of the ingredient to add to the concrete mixture based on real-time particle analysis of the ingredient from the particle analyzing system 104. In some implementations, concrete preparation system 100 can be retrofit to a traditional ready-mix concrete plant. For example, adding the concrete preparation system 100 to a ready-mix plant may allow the ready-mix plant to more precisely tailor concrete mixes for specific applications and job sites.

The particle analyzing system 104 can include various different sensors configured to measure various characteristics of concrete ingredients. For example, the sensors used by the particle analyzing system 104 can include, but are not limited to, optical sensors (e.g., visible light cameras, infrared cameras, dynamic optical microscopy sensors) and mechanical sensors (e.g., sieves, sedigraphs, impact hammer, electrodynamic vibrator). The measurement data is used by the control system 102 to determine characteristics of the ingredients of the concrete mixture. For example, ingredient characteristics can include, but are not limited to, particle sizes, particle shapes, surface areas, and particle sphericity.

The sensors of the particle analyzing system 104 are arranged to obtain measurement data of concrete ingredients as the ingredients are added to a concrete mixture. For example, in some implementations optical sensors can be arranged in an array along a conveyor or a chute used to convey the raw ingredients to the mixing vessel 110. The optical sensors can transmit images of the ingredients to the control system 102, which (as explained in more detail below) can use image processing algorithms to identify particle shapes and sizes.

Some implementations may include a series of sieves to separate particles of an ingredient by size. In such implementations, the optical sensors can be positioned proximate to each sieve to capture images of the particles passing through the sieve. The images can then be used, for example, to determine an approximate count of each size range of particles exiting each sieve. In such implementations, the separated particles may be recombined before being added to the mixing vessel 110.

The concrete mix sensors 106 provide rheometry measurements of the concrete mixture to the control system 102. For example, the concrete mix sensors 106 can measure various attributes of the concrete mixture that can be used to estimate or compute rheumatic properties of the concrete mixture in real-time. The concrete mix sensors 106 can include, but are not limited to, viscosity sensors, rheometers, temperature sensors, moisture sensors, ultrasonic sensors (e.g., ultrasonic pulse velocity sensors), electrical property sensors (e.g., electrodes, electrical resistance probes), electromagnetic sensors (e.g., short-pulse radar), or other sensors (e.g., geophone, accelerometer). The concrete mix sensors 106 can include, but are not limited to, hydrophobicity, moisture content, XRD spectra, XRF spectra, static yield stress, acoustic impedance, p-wave speed, dynamic yield stress, static modulus of elasticity, Young's modulus, bulk modulus, shear modulus, dynamic modulus of elasticity (DME), Poisson's ratio, density, resonance frequency, nuclear magnetic resonance (NMR), dielectric constant, electric resistivity, polarization potential, and capacitance.

For example, viscosity, moisture, and temperature sensors can be installed in the mixing vessel 110. These sensors can be used to measure rheological properties of the concrete mixture such as changes in the viscosity of the mixture over time and at different moisture content levels and temperatures. As described in more detail below, the control system 102 can use the rheometry measurements to determine whether and how much additional ingredients should be added to the concrete mixture to obtain desired concrete properties.

Post-curing characteristics can be determined from rheometry measurements by, e.g., using multi-dimensional lookup tables relating experimentally obtained post-curing characteristics to mixtures with known rheological properties, by applying theoretical and analytical particle packing model-based Bayesian optimization algorithms to the rheometry measurements, or a combination thereof.

In some examples, rheometry measurements can be performed on the initial concrete mixture. Rheometry measurements of the concrete mixture with the ingredients added can be estimated based on the measured characteristics of the ingredients. The rheometry measurements are used to predict characteristics of the concrete after curing.

The actual rheometry measurements of the concrete mixture can be obtained and compared with the estimated rheometry to determine whether to add additional ingredients. The system can determine, based on the rheometry measurements, whether the concrete mixture is likely to achieve a desired set of post-curing characteristics. If not, the initial mixture is adjusted through an iterative process until the rheometry measurements indicate that the concrete mixture is likely to achieve the desired post-curing characteristics.

During the iterative adjustment process, portions of concrete ingredients are incrementally added to the initial concrete mixture while changes in the rheometry measurements are monitored. Additional portions of ingredients are added until the rheometry measurements indicate that the concrete mixture is likely to achieve the desired post-curing characteristics. Such post-curing characteristics can include, but are not limited to, compressive strength, tensile/flexural strength, flowability, toughness, cure time, cure profile, finish, density (wet & dry), thermal insulation, shrinkage, and slump.

In some examples, actual performance of the concrete mixture can be compared with the predicted performance. A discrete element method (DEM) simulator can then be updated and/or trained based on the difference between the actual performance and the predicted performance.

Figure 2:
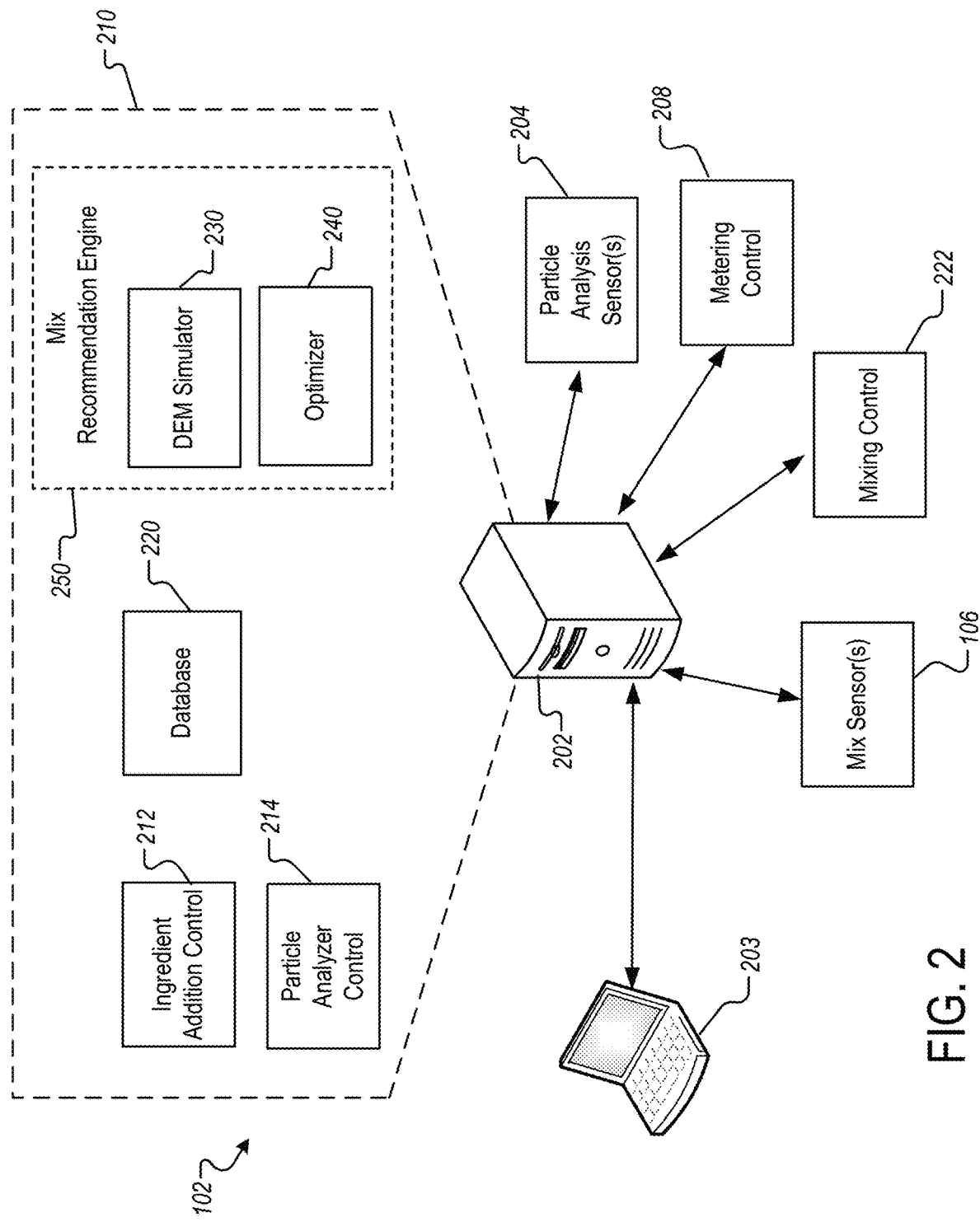
FIG. 2 depicts a block diagram of an exemplary control system for the concrete preparation system of FIG. 1.

FIG. 2 is a block diagram of an exemplary control system 102 for the concrete preparation system 100. The system 102 includes a computing system 202 in communication with the concrete mix sensors 106, particle analysis sensors 204 of the particle analyzing system 104, a metering control system 208 which can control operations of the ingredient metering system 108. Computing system 202 is configured to control various aspects of the concrete preparation process. For example, computing system 202 can store and execute one or more computer instruction sets to control the execution of aspects of the concrete preparation processes described herein. Computing system 202 can include a system of one or more computing devices. The computing devices can be, e.g., a system of one or more servers. For example, a first server can be configured to receive and process data from the concrete mix sensors 106 and the particle analysis sensors 204. Another server can be configured to interface with the metering control system 208 and issue control commands based on analysis results from the first server.

In some implementations, the computing system 202 can be operated or controlled from a user computing device 203. User computing device 203 can be a computing device, e.g., desktop computer, laptop computer, tablet computer, or other portable or stationary computing device.

Briefly, computing system 202 can control the overall concrete preparation system 100 to prepare concrete mixtures. The computing system 202 can use the particle analysis sensors 204 to characterize concrete ingredients as they are added to a concrete mixture.

The computing system 202 obtains rheometry measurements from the mix sensors 106 as the concrete mixture is mixed in the mixing vessel 110. The system compares the rheometry measurements with estimated rheometry measurements to determine, e.g., whether the concrete mixture will meet desired post-curing mechanical properties or whether additional ingredients should be added.

In some implementations, computing system 202 can include a set of operations modules 210 for controlling different aspects of a concrete additive manufacturing process. The operation modules 210 can be provided as one or more computer executable software modules, hardware modules, or a combination thereof. For example, one or more of the operation modules 210 can be implemented as blocks of software code with instructions that cause one or more processors of the computing system 202 to execute operations described herein. In addition or alternatively, one or more of the operations modules can be implemented in electronic circuitry such as, e.g., programmable logic circuits, field programmable logic arrays (FPGA), or application specific integrated circuits (ASIC). The operation modules 210 can include an ingredient addition controller 212, a particle analyzer controller 214, DEM simulator 230, an optimizer 240, and one or more databases 220.

Ingredient addition controller 212 interfaces with the metering control system 208 to control the addition of ingredients to the concrete mixing vessel 110. For example, the ingredient addition controller 212 can issue commands from the computing system 202 to the metering control system 208 to control the addition of ingredients to the concrete mixture in the mixing vessel 110.

Particle analyzer control 214 interfaces with the particle analysis sensors 204 of the particle analyzing system 104. Particle analyzer controller 214 receives and buffers data from the particle analysis sensors 204. The particle analyzer controller 214 can process the sensor data to determine particle characteristics of each analyzed ingredient. For example, as discussed in more detail below, the particle analyzer controller 214 can execute data analysis algorithms to interpret the sensor data and determine particle characteristics including, but not limited to, particle sizes, particle shapes, and particle surface areas.

The computing system 202 includes a mix recommendation engine 250. The mix recommendation engine 250 includes a DEM simulator 230 and an optimizer 240. Operations of mix recommendation engine 250 will be described in greater detail with reference to FIGS. 3 and 4.

The control system can employ DEM simulator 230 to estimate the rheometry parameters of a given concrete mixture based on the particle characteristics of the ingredients. For example, the DEM simulator 230 can employ database 220 to determine estimated rheometry measurements. The computing system can include a database 220 that correlates concrete particle characteristics to experimentally determined rheometry parameters. In some implementations, the DEM simulator 230 includes algorithms that estimate particle packing efficiencies from the particle parameters and a database 220 that correlates particle packing efficiencies with experimentally determined rheometry parameters. The computing system 202 can then compare the estimated particle packing efficiencies to the data in the database 220 to estimate the rheometry parameters of the concrete mixture.

In some implementations, DEM simulator 230 included a packing efficiency model to determine a packing efficiency of the ingredients based on the particle characteristics. The model can be a theoretical and analytical particle packing model-based Bayesian optimization algorithm—or other machine learning model—to determine a packing efficiency of the particles and estimate rheometry parameters of the mixture.

In some implementations, the DEM simulator 230 can include a machine learning model to estimate particle packing efficiency and/or rheometry parameters for a concrete mixture from measured particle characteristics. For example, the machine learning model can include a model that has been trained on experimental data to receive particle characteristics of concrete ingredients as input, and to generate a predicted output, e.g., an estimate of the particle packing efficiency, an estimate of rheometry parameters for a concrete mixture, or both. In some implementations, the machine learning model is a deep learning model that employs multiple layers of models to generate an output for a received input. A deep neural network is a deep machine learning model that includes an output layer and one or more hidden layers that each applies a non-linear transformation to a received input to generate an output. In some cases, the neural network may be a recurrent neural network. A recurrent neural network is a neural network that receives an input sequence and generates an output sequence from the input sequence. In particular, a recurrent neural network uses some or all of the internal state of the network after processing a previous input in the input sequence to generate an output from the current input in the input sequence. In some other implementations, the machine learning model is a convolutional neural network. In some implementations, the machine learning model is an ensemble of models that may include all or a subset of the architectures described above.

In some implementations, the machine learning model can be a feedforward autoencoder neural network. For example, the machine learning model can be a three-layer autoencoder neural network. The machine learning model may include an input layer, a hidden layer, and an output layer. In some implementations, the neural network has no recurrent connections between layers. Each layer of the neural network may be fully connected to the next, there may be no pruning between the layers. The neural network may include an ADAM optimizer, or any other multi-dimensional optimizer, for training the network and computing updated layer weights. In some implementations, the neural network may apply a mathematical transformation, such as a convolutional transformation, to input data prior to feeding the input data to the network.

In some implementations, the machine learning model can be a supervised model. For example, for each input provided to the model during training, the machine learning model can be instructed as to what the correct output should be. The machine learning model can use batch training, training on a subset of examples before each adjustment, instead of the entire available set of examples. This may improve the efficiency of training the model and may improve the generalizability of the model. The machine learning model may use folded cross-validation. For example, some fraction (the "fold") of the data available for training can be left out of training and used in a later testing phase to confirm how well the model generalizes. In some implementations, the machine learning model may be an unsupervised model. For example, the model may adjust itself based on mathematical distances between examples rather than based on feedback on its performance.

A machine learning model can be trained to estimate rheometry parameters for concrete mixtures based on measured characteristics of the ingredients to the mixture. In some examples, the machine learning model can be trained on experimentally determined data relating known characteristics of concrete ingredients to experimentally determined rheometry parameters.

The computing system 202 can store one or more databases 220 that correlate different measured parameters to experimentally determined characteristics of a concrete mixture or post-curing concrete. For example, the database 220 can include a lookup table correlating desired post-curing concrete characteristics to concrete mixture rheometry parameters, a lookup table correlating ingredient characteristics to particle packing efficiencies, and a lookup table correlating ingredient characteristics to mixture remoter parameters. Each lookup table can be a multi-dimensional data structure containing measurable concrete parameters, concrete mixture parameters, or ingredient characteristics to experimentally determined parameters.

Figure 3:
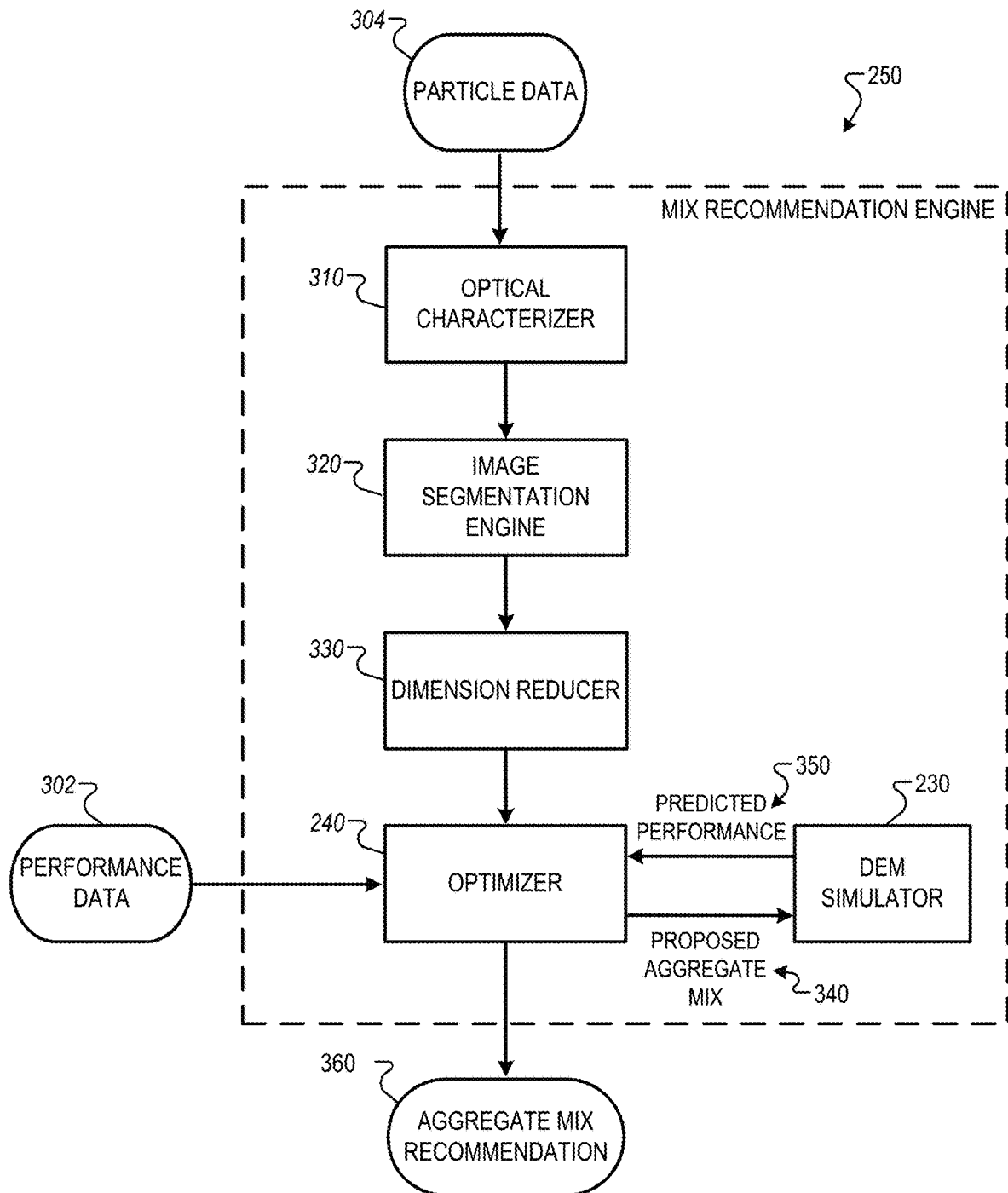
FIG. 3 depicts a block diagram of an example mix recommendation engine.

FIG. 3 illustrates a block diagram of an example mix recommendation engine 250. The mix recommendation engine 250 receives, as input, particle data 304. The particle data 304 can include sensor data from the particle analysis sensors 204. The mix recommendation engine 250 also receives, as input, performance data 302 indicating required performance characteristics of an aggregate mix. The mix recommendation engine can be used to create recipes that meet strength, workability, and durability requirements by confining proposed gradation into empirical curves.

The mix recommendation engine 250 includes an optical characterizer 310 including high precision optical characterizer hardware. The optical characterizer characterizes the particle data 304. Characteristics can include but are not limited to: dimensions, elongation, flatness, length of three axes, volume, surface area. The mix recommendation engine 250 also includes an image segmentation engine 320 for performing image segmentation and analysis on the particle data 304.

The mix recommendation engine 250 includes a dimension reducer 330. The dimension reducer 330 performs extraction of reduced dimensional, or lower dimensional, physical characteristics of the particle data 304. Dimension reduction is beneficial for analyzing the highly irregular geometry of aggregate due to the large number of particles in the system. In some examples, the extracted lower dimensional characteristics generated by the dimension reducer 330 can be used to regularize a multisphere approximation from an auto encoder. In some examples, the extracted lower dimensional characteristics or properties can be used to directly generate statistically similar models from databases, e.g., database 220. The lower dimensional characteristics can include, for example, elongation, flatness, angularity, sphericity, aspect ratio, and other characteristics.

The optimizer 240 receives the lower dimensional characteristics from the dimension reducer 330. The optimizer 240 generates a proposed aggregate mix 340 based on the lower dimensional characteristics and the performance data 302. The optimizer 240 provides the proposed aggregate mix 340 to the DEM simulator 230. The DEM simulator 230 determines a predicted performance 350 of the proposed aggregate mix 340.

The DEM simulator 230 outputs the predicted performance 350 to the optimizer 240. The optimizer 240 can compare the predicted performance 350 to the performance data 302. If the predicted performance 350 satisfies requirements of the performance data 302, the optimizer 240 outputs the proposed aggregate mix 340 as an aggregate mix recommendation 360. If the predicted performance 350 does not satisfy requirements of the performance data 302, the optimizer 240 can revise the recipe and provide a new proposed aggregate mix 340 to the DEM simulator 230. The optimizer 240 can continue to generate new proposed aggregate mixes 340 until the predicted performance 350 satisfies criteria specified by the performance data 302.

The mix recommendation engine 250 outputs the aggregate mix recommendation 360 including a recommended recipe for mixing the particles. The computing system 202 can use the aggregate mix recommendation 360 to adjust the ingredient addition controller 212. The ingredient addition controller 212 can then control addition of ingredients to the concrete mixing vessel 110 based on the aggregate mix recommendation 360.

Figure 4A:
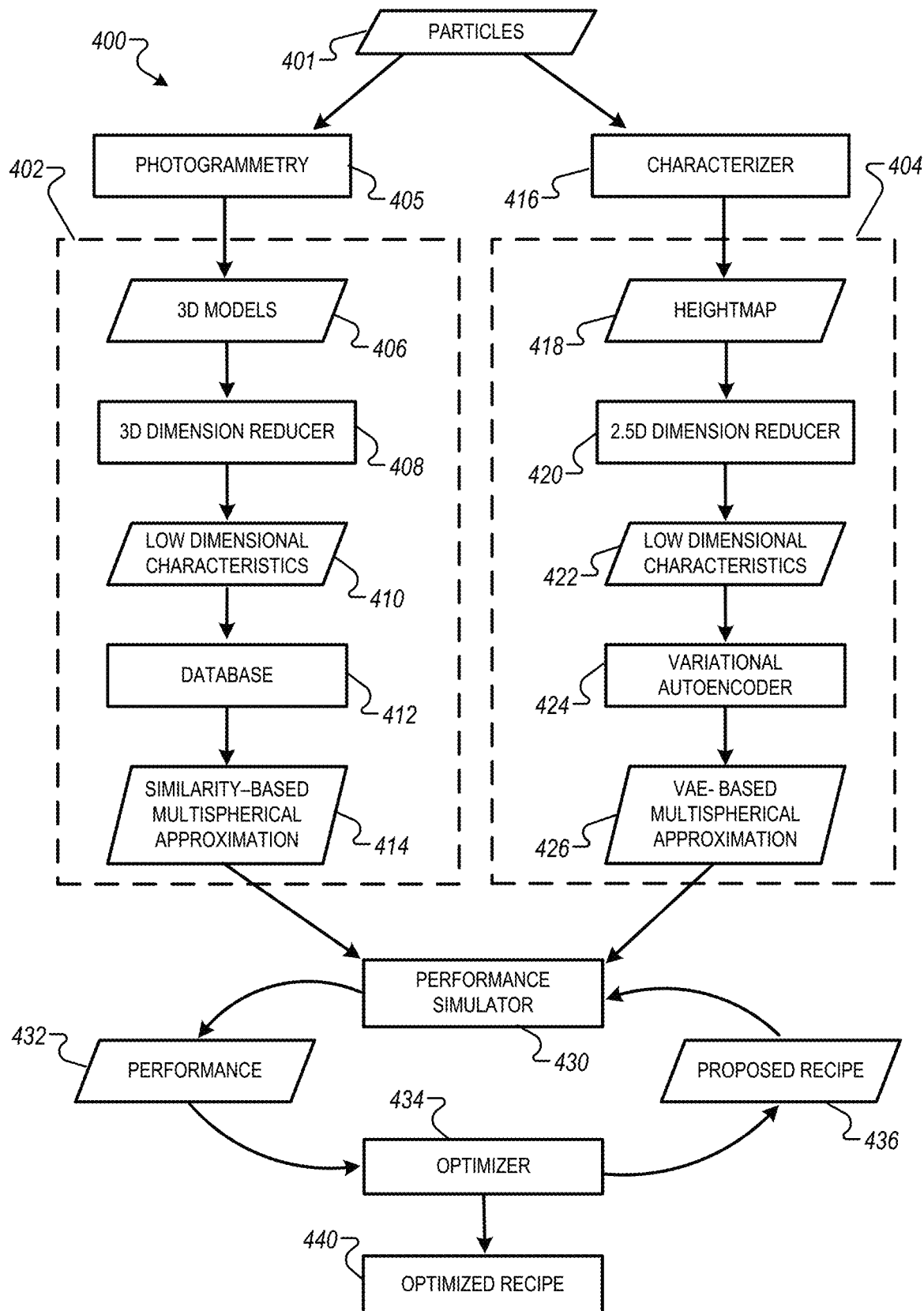
FIG. 4A illustrates example processes for generating multispherical approximations for aggregate mix modeling.
Figure 4B:
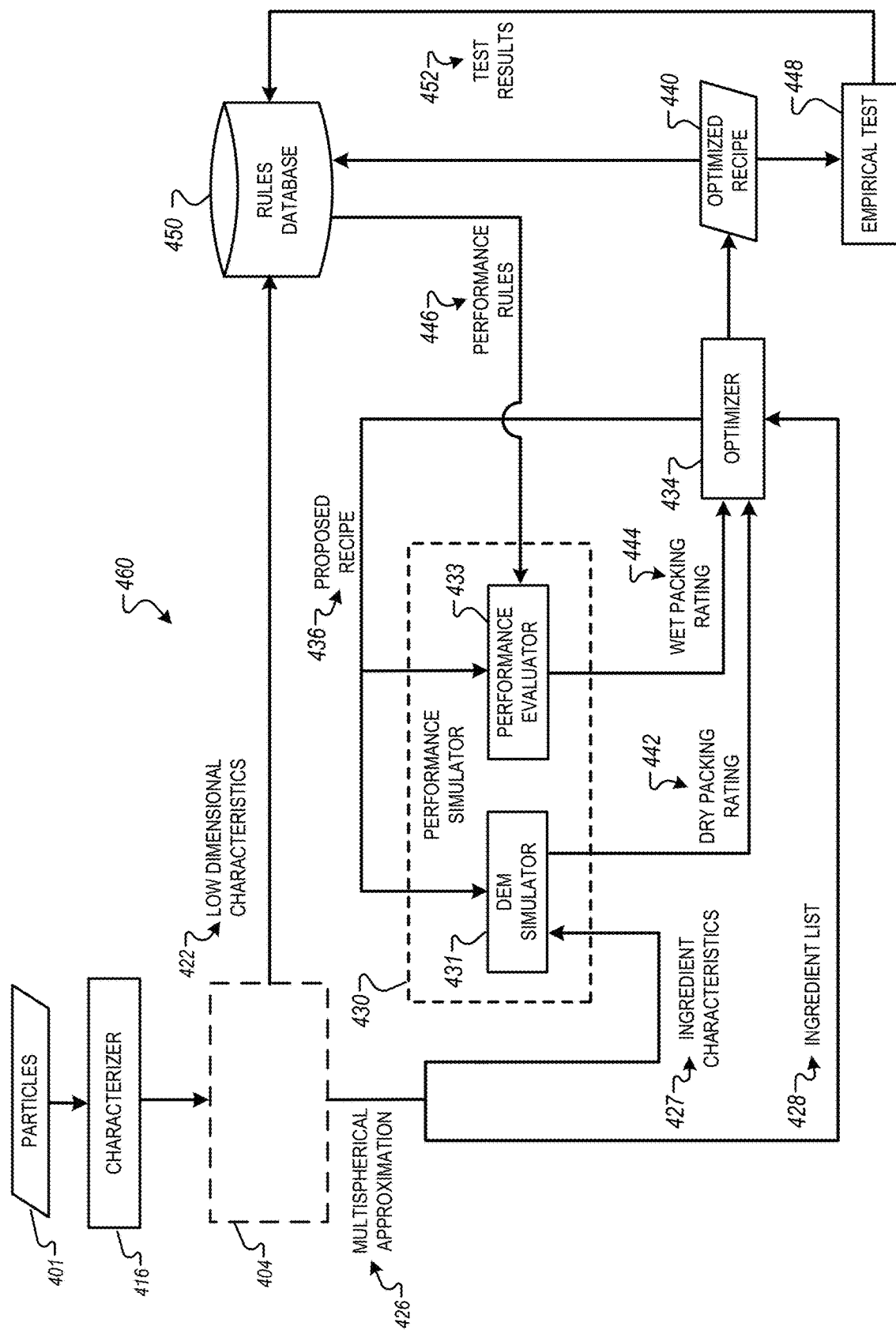
FIG. 4B illustrates example processes for producing an evolving concrete mixture heuristic.

FIG. 4A illustrates an example process 400 for generating multispherical approximations for aggregate mix modeling, FIG. 4B illustrates an example process 460 for producing an evolving concrete mixture heuristic.

Referring to FIG. 4A, simulating polyhedra with flat polygonal faces, straight edges and sharp vertices can be computationally expensive. Multi-spherical approximation of non-spherical particles can be employed to enable simplicity of modeling and simulation while preserving physics properties.

Parameters for multisphere generation can be learned by machine learning models such as an encoder/decoder network. The parameters can then be fed into a generation algorithm. A multispherical approximation approach is based on clumps, clusters, or clouds of overlapping smaller spheres to represent a larger nonspherical irregular shape, in which internal contacts are ignored and the cluster behaves as a rigid body. Each sphere can be defined by a center coordinate location and a radius. For example, a sphere can be defined by an x-y-z coordinate of the center of the sphere, and a radius of the sphere extending from the center.

A multispherical approximation can be used to reduce resolution or fidelity of a digital representation of an object such as a particle. For example, a high fidelity digital representation of a particle can include hundreds or thousands of points and/or lines. The points and lines can approximate the surface of the particle with high accuracy. In contrast, a multispherical approximation can include tens or dozens of spheres to represent the same particle. Thus, lower fidelity digital representations, or simulations, of particles can be used, where the lower fidelity digital representations can be geometrically similar to the original characterizations.

Process 400 includes two alternative sub-processes 402 and 404 for generating low dimensional approximations of aggregates to simulate the particles. The simulated particles can be created by trained variational auto encoding (sub-process 404) or by similarity-based recommendation from a database of characterized materials (sub-process 402), or a combination of both sub-processes. The simulated particles can capture features that, during performance simulation, produce statistically similar behaviors to higher fidelity digital representations.

Referring to sub-process 402, in some examples, photogrammetry scanning 405 is used to generate highly accurate 3D models 406 (e.g., a surface mesh) of particles 401. The photogrammetry 3D models 406 can be applied to a 3D dimension reducer 408 which generates lower dimensional physical characteristics 410 of the particles 401. The dimension reducer 408 extracts the lower dimensional physical characteristics 410 from the 3D models 406. For instance, the dimension reducer 408 can characterize the particles 401 according to the elongation, flatness, angularity, and sphericity of the particles. The lower dimensional physical characteristics 410 output by the dimension reducer 408 can be compared with entries in a particle simulation database (e.g., database 412) to select a set of one or more similarity-based multispherical approximations 414 that best match the particles 401.

Referring to sub-process 404, in some examples, instead of or in addition to sub-process 402, an autoencoder such as a variational autoencoder can be trained to map a scanned particle 401 into latent space, and then decode the mapped particle to multisphere coordinates and radius. The lower dimensional physical characteristics can be used to regularize the latent space, which increases the convergence speed as well as interpretability. The lower dimensional physical characteristics can include, for example, geometry, gradation, and texture for the aggregate particles.

A characterizer 416 can be used to scan aggregate particles 401 to generate a high resolution optical characterization of the particles. For example, the characterizer 416 can include two sets of charge-coupled device (CCD) hardware and computer vision software. The resulting heightmap 418 contains partial information about top surface texture and geometry (e.g., a 2.5 dimensional (2.5D) representation of the particles).

The heightmap 418 can be used to infer characterizations of the physical properties of the aggregate particles 401. A 2.5D dimension reducer 420 can extract physical characteristics, e.g., lower dimensional characteristics 422, from the heightmap 418. The lower dimensional characteristics 422 can include any of the following shape factors: size distribution, shape distribution, aspect ratios, flatness, aspect ratio, convexity, jaggedness, roundness, sphericity, and/or angularity.

A multispherical approximation of particles is generated. The multispherical approximation can be generated, e.g., by a physics regularized auto-encoder to produce a variational autoencoder (VAE)-based multispherical approximation 426 or by a similarity-based recommendation to produce a similarity-based multispherical approximation 414. For example, a variational autoencoder 424 can generate a VAE-based multispherical approximation 426 based on the lower dimensional characteristics 422. The multispherical approximations 414, 426 can then be used to perform simulation and optimization in order to identify aggregate mixtures that satisfy performance requirements. In some examples, results of the sub-process 402 and the sub-process 404 can be used to cross-validate one another.

Mixture optimization can be performed by simulating a mixture using the lower dimensional approximation of one or more aggregates. For example, mixture optimization can be performed using a performance simulator 430 including, for example, a Bayesian inference network and/or a DEM physics simulator. The DEM simulator is a physics modeling method that can simulate static packing behavior and rheology (e.g., dynamic flow behavior). Optimization can be performed using a closed loop control system between the Bayesian inference network and the DEM simulator. The Bayesian network can predict exploration/exploitation actions as a function of uncertainty in lower feature space, while the DEM engine simulates high fidelity physical experiments and provides feedback results to a learning algorithm to iteratively improve the approximation.

To perform optimization, the performance simulator 430 uses the multispherical approximations 414, 426 to evaluate performance 432 of a proposed recipe 436. The optimizer 434 determines new proposed recipes 436 based on the performance 432. The optimization is performed until a recipe is achieved that satisfies performance criteria. When a recipe is achieved that satisfies performance criteria, the optimizer 434 outputs the optimized recipe. Optimization processes are described in greater detail with reference to FIG. 4B.

FIG. 4B illustrates an example process 460 for producing an evolving concrete mixture heuristic. In some examples, the process 460 is performed by the mix recommendation engine 250. The process 460 can be implemented to design modified empirical methods (e.g. tarantula curves, coarseness factor, etc.) that take into account the geometrical features of aggregate particles.

The process 460 includes sub-process 404 for generating VAE-based multispherical approximations 426, as described with reference to FIG. 4A. In some examples, instead of the sub-process 404, the sub-process 402 can be used to generate similarity-based multispherical approximations 414. While the processes of FIG. 4B will be described as using the VAE-based multispherical approximation 426, the disclosed processes can also be implemented using the similarity-based multispherical approximations 414.

The multispherical approximation 426 includes approximations of ingredients of each multisphere. An ingredient can be, for example, a smaller sphere of the multisphere. Ingredients can be classified by ingredient characteristics 427, such as a coordinate location and a radius for each sphere. The DEM simulator 431 receives the ingredient characteristics 427.

The optimizer 434 receives an ingredient list 428, including a list of the spheres of each multi sphere. The ingredient list 428 can include a percentage of the multisphere that is represented by each smaller sphere. The optimizer 434 generates a proposed recipe 436 based on the ingredient list 428.

The performance simulator 430 predicts the performance 432 of the proposed recipe 436 by determining a dry packing rating 442 and a wet flowability rating 444 of the proposed recipe 436. The performance simulator 430 includes the DEM simulator 431 and the performance evaluator 433.

The DEM simulator 431 is a physics simulator. The DEM simulator 431 can use the ingredient characteristics 427 of the approximated multispherical models to predict whether the proposed concrete recipe will satisfy dry packing performance requirements. The DEM simulator 431 outputs a dry packing rating 442 to the optimizer 434.

Dry packing can be measured based on a predicted void fraction, or void percentage, for the proposed recipe. The void fraction can be determined based on the volume of non-aggregate content (e.g., cement paste) over the total aggregate and cement mixture volume. In some examples, the dry packing rating can correspond to a cured packing density of the cement mixture. In some examples, a dry packing rating can be a value from 0.0 to 1.0, In general, a higher dry packing (e.g., a dry packing rating closer to 1.0) is preferable over a lower dry packing rating.

Performance rules applicable to the particles are selected. The performance evaluator 433 selects performance rules 446 from a rules database 450. The performance evaluator 433 evaluates flowability performance of the proposed recipe 436 based on the performance rules 446. The performance rules 446 can be, for example, empirical rules establishing limits for flowability of various mixing proportions. In some examples, the performance rules 446 can include tarantula curves and/or coarseness factor charts. Since wet flowability ratings are not monotonic, the ratings can be plotted as isolines (e.g., contour lines) in a graph of different size aggregate proportions, called a tarantula curve. In some examples, a tarantula curve can be a graph of percent retained aggregate vs. sieve size. A coarseness factor chart can be a graph of coarseness factor vs. workability. The performance rules 446 can establish static limits for upper and lower bounds for gradations.

The performance evaluator 433 can select performance rules 446 appropriate for the set of particles, based on the low dimensional characteristics 422. For example, the performance rules 446 can be specific to different particle geometries, shapes, sizes and/or textures. The performance evaluator 433 can use the selected empirical rules to determine whether a proposed recipe 436 will likely satisfy wet flowability performance requirements. The performance evaluator 433 determines a wet flowability rating 444 of the proposed recipe 436 based on the performance rules 446. The performance evaluator 433 outputs the wet flowability rating 444 to the optimizer 434.

Wet packing of particles is determined by particle size and shape in interaction with the cement paste in a concrete mixture. Wet packing affects a mixture's rheology (e.g., shearing stress over shearing strain). The rheology can affect the mixture's workability, flowability, and pumpability. Wet flowability can be measured with a slump test. The result of the slump test is a measure in the distance of slump from an original cone height to a released slumped state. Different applications require different degrees of slump from very stiff (low slump) to more liquid (higher slump). In general, the wet flowability rating is a range from zero to twelve inches. An example of an acceptable wet flowability rating is a four-inch slump.

The wet flowability and dry packing performance of a proposed recipe for a concrete mixture formed from the particles is predicted. For example, the dry packing rating 442 and the wet flowability rating 444 can be provided to the optimizer 434. The optimizer 434 can be, for example, a Bayesian optimizer. The optimizer 434 can determine, based on the wet flowability rating 444 and the dry packing rating 442, whether the proposed concrete recipe is likely to satisfy performance criteria. Based on determining that the proposed recipe will not likely satisfy performance criteria, the optimizer 434 can propose a new proposed recipe 436.

The proposed recipe is altered iteratively until the predicted wet flowability and dry packing performance satisfy performance criteria. For example, the optimizer 434 can perform a number of iterations to optimize the recipe. For example, the optimizer 434 can continue to iteratively alter the proposed recipes in order to achieve a highest dry packing rating 442 subject to an acceptable wet flowability rating 444. In some examples, the optimizer 434 can continue to iteratively alter the proposed recipes in order to achieve the highest combined dry packing rating 442 and wet flowability rating 444.

A final recipe for the concrete mixture is output. For example, based on determining that the proposed recipe will likely satisfy performance criteria, the optimizer 434 can output a final, optimized concrete recipe 440. The optimized recipe 440 can be used to create a concrete mixture.

Empirical tests 448 can be performed on the optimized recipe 440 to determine test results 452. Based on the test results 452, the empirical rules of the rules database 450 can be updated. The rules database 450 can be updated based on the lower dimensional characteristics 422, the optimized recipe 440, and the test results 452. In this way, the empirical rules in the rules database 450 can be tuned for the various aggregate particle characteristics, improving accuracy of the performance simulations.

In some examples, the empirical rules are updated by adding a tarantula curve to the rules database 450 that is designated for use when the particle characteristics match the lower dimensional characteristics 422. In some examples, the empirical rules are updated by adjusting a tarantula curve of the rules database 450. In some examples, the updated empirical rules can be incorporated into the optimizer 434. The optimizer 434 can then use the updated empirical rules to evaluate and optimize future recipes.

Figure 5:
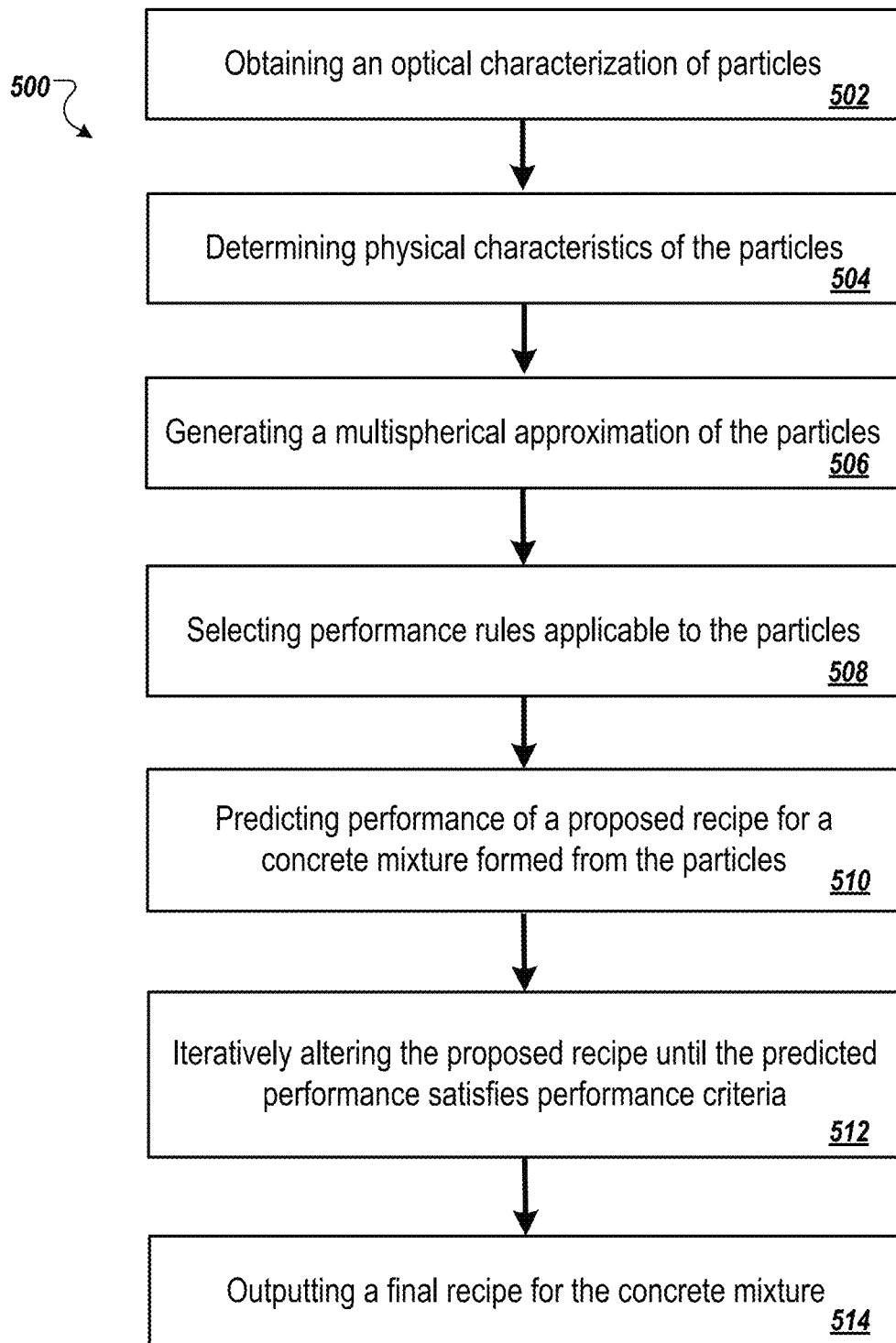
FIG. 5 is a flow chart of an example process for optimizing a concrete mixture recipe.

FIG. 5 is a flow diagram that illustrates a process 500 for optimizing a concrete mixture recipe. The process 500 can be performed by one or more computing devices. For example, as discussed above, the process 500 may be performed by computing system 202 of FIG. 2. Process 500 employs various aspects of processes 400 and 460 described above in reference to FIGS. 4A and 4B.

The process 500 includes obtaining an optical characterization of particles (502). For example, as described with reference to FIG. 4A, the optical characterization can be obtained by scanning the particles 401 using photogrammetry 405 or a characterizer 416. The optical characterization can be a 3D model 406 or a heightmap 418.

The process 500 includes determining physical characteristics of the particles (504). For example, as described with reference to FIG. 4A, in sub-process 402, the 3D dimension reducer 408 can obtain lower dimensional characteristics 410 from the 3D models 406. In sub-process 404, the 2.5D dimension reducer 420 can obtain lower dimensional characteristics 422 from the heightmap 418.

The process 500 includes generating a multispherical approximation of the particles (506). For example, as described with reference to FIG. 4A, in sub-process 402, a similarity-based multispherical approximation 414 is obtained from a database 412 based on the lower dimensional characteristics 410. In sub-process 404, a variational encoder 424 produces a VAE-based multispherical approximation 426 from the lower dimensional characteristics 422.

The process 500 includes selecting performance rules applicable to the particles (508). For example, as described with reference to FIG. 4B, the performance rules 446 are selected from the rules database 450 based on the lower dimensional characteristics 422.

The process 500 includes predicting performance of a proposed recipe for a concrete mixture formed from the particles (510). For example, as described with reference to FIG. 4B, the performance simulator 430 predicts performance of the proposed recipe 436 formed from the particles 401, as specified by the ingredient list 428.

The process 500 includes iteratively altering the proposed recipe until the predicted performance satisfies performance criteria (512). For example, as described with reference to FIG. 4B, the DEM simulator of the performance simulator 430 determines a dry packing rating 442 based on the ingredient characteristics 427. The performance evaluator 433 of the performance simulator 430 determines a wet flowability rating 444 based on the performance rules 446. The optimizer 434 iteratively outputs proposed recipes 436 until the dry packing rating 442 and the wet flowability rating 444 satisfy performance criteria.

The process 500 includes outputting a final recipe for the concrete mixture (514). For example, as described with reference to FIG. 4B, when performance criteria is satisfied, the optimizer 434 outputs the optimized recipe 440. The rules database 450 can then be updated based on test results 452 of empirical tests 448 performed on the optimized recipe 440.

In summary, when a new recipe for a concrete mixture is proposed, a weight percent retained curve can be generated based on the optical characterization of the particles. The percent retained curve contains the valuable geometry information. The empirical fusion adds a heuristic boundary to the percent retained curve in order to eliminate unnecessary simulations before the simulation/optimization loop and expedite the recipe recommendation.

The disclosed techniques can be modified to apply to different geological regions. For example, the performance evaluator 433 can retrieve appropriate empirical curves for the characteristics of the particles. The empirical rules of the rules database 450 are adjusted and adapted for shape-specific gradations, for example, the boundaries of the tarantula curves can be updated for different shapes from the tuned physical simulation results. As previously mentioned, each percent retained curve from the characterizer 416 not only produces gradation information, but also is geometry and texture specific. Therefore, the modified tarantula curve can be projected into the other dimensions of geometry texture, creating the relationship between workability, gradation, and aggregate shapes in a multidimensional graph. By considering shape factors and texture in determining optimized mixtures, material availability can be expanded, energy consumption can be reduced, and structural durability can be increased.

Figure 6:
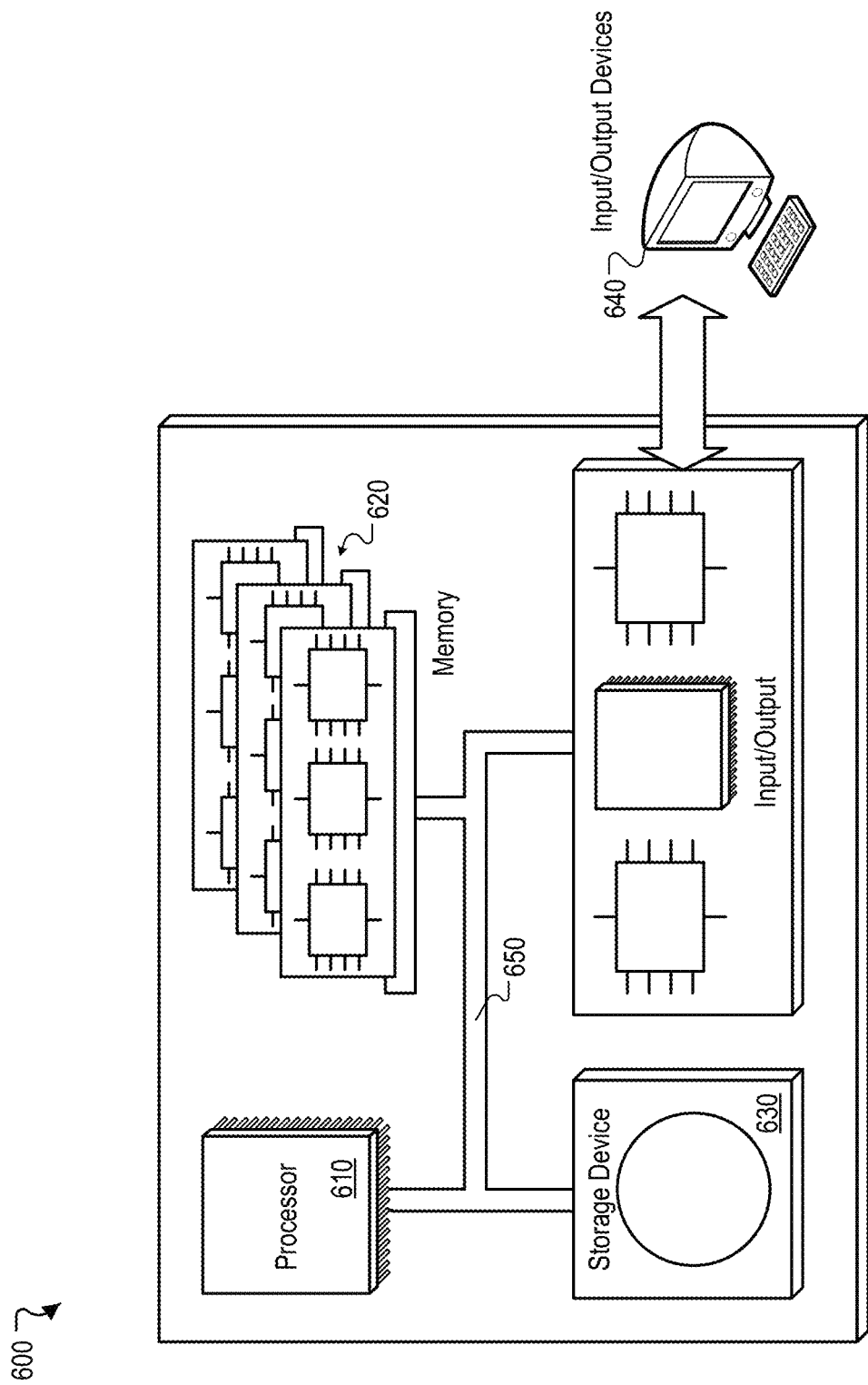
FIG. 6 depicts a schematic diagram of a computer system that may be applied to any of the computer-implemented methods and other techniques described herein.

FIG. 6 is a schematic diagram of a computer system 600. The system 600 can be used to carry out the operations described in association with any of the computer-implemented methods described previously, according to some implementations. In some implementations, computing systems and devices and the functional operations described in this specification can be implemented in digital electronic circuitry, in tangibly-embodied computer software or firmware, in computer hardware, including the structures disclosed in this specification (e.g., system 600) and their structural equivalents, or in combinations of one or more of them. The system 600 is intended to include various forms of digital computers, such as laptops, desktops, workstations, personal digital assistants, servers, blade servers, mainframes, and other appropriate computers, including vehicles installed on base units or pod units of modular vehicles. The system 600 can also include mobile devices, such as personal digital assistants, cellular telephones, smartphones, and other similar computing devices. Additionally, the system can include portable storage media, such as Universal Serial Bus (USB) flash drives. For example, the USB flash drives may store operating systems and other applications. The USB flash drives can include input/output components, such as a wireless transducer or USB connector that may be inserted into a USB port of another computing device.

The system 600 includes a processor 610, a memory 620, a storage device 630, and an input/output device 640. Each of the components 610, 620, 630, and 640 are interconnected using a system bus 650. The processor 610 is capable of processing instructions for execution within the system 600. The processor may be designed using any of a number of architectures. For example, the processor 610 may be a CISC (Complex Instruction Set Computers) processor, a RISC (Reduced Instruction Set Computer) processor, or a MISC (Minimal Instruction Set Computer) processor.

In one implementation, the processor 610 is a single-threaded processor. In another implementation, the processor 610 is a multi-threaded processor. The processor 610 is capable of processing instructions stored in the memory 620 or on the storage device 630 to display graphical information for a user interface on the input/output device 640.

The memory 620 stores information within the system 600. In one implementation, the memory 620 is a computer-readable medium. In one implementation, the memory 620 is a volatile memory unit. In another implementation, the memory 620 is a non-volatile memory unit.

The storage device 630 is capable of providing mass storage for the system 600. In one implementation, the storage device 630 is a computer-readable medium. In various different implementations, the storage device 630 may be a floppy disk device, a hard disk device, an optical disk device, or a tape device.

The input/output device 640 provides input/output operations for the system 600. In one implementation, the input/output device 640 includes a keyboard and/or pointing device. In another implementation, the input/output device 640 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touchscreen flat-panel displays and other appropriate mechanisms.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

As used herein, the term "ready mix" refers to concrete that is batched for delivery from a central plant instead of being mixed on a job site. Typically, a batch of ready mix is tailor-made according to the specifics of a particular construction project and delivered in a plastic condition, usually in cylindrical trucks often referred to as "concrete mixers."

As used herein, the term "real-time" refers to transmitting or processing data without intentional delay given the processing limitations of a system, the time required to accurately obtain data, and the rate of change of the data. Although there may be some actual delays, the delays are generally imperceptible to a user.

While this specification contains many specific implementation details, these should not be construed as limitations on the scope of what is being claimed, which is defined by the claims themselves, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claim may be directed to a subcombination or variation of a subcombination.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method of generating a recipe for a concrete mixture, comprising:
    determining, based on sensor measurements of a set of particles, physical characteristics of the set of particles;
    generating, based on the physical characteristics, a multispherical approximation of the set of particles;
    predicting performance of a proposed recipe for a concrete mixture formed from the set of particles to obtain a predicted performance by determining a wet flowability rating of the proposed recipe based on performance rules relevant to the physical characteristics of the set of particles, and determining a dry packing rating of the proposed recipe based on the multispherical approximation; and
    outputting a final recipe based on the proposed recipe.

2. The method of claim 1, wherein determining the physical characteristics comprises:
generating, from the sensor measurements, three dimensional (3D) models of the particles; and
determining the physical characteristics from the 3D models.

3. The method of claim 2, wherein the physical characteristics comprise one or more of: particle elongation, particle flatness, particle angularity, or particle sphericity.

4. The method of claim 1, wherein generating the multispherical approximation comprises selecting, using the physical characteristics, a set of one or more multispherical approximations of the particles from a database comprising a plurality of multispherical approximations indexed based on different physical characteristics.

5. The method of claim 1, wherein determining the physical characteristics comprises:
generating, from the sensor measurements, heightmap representations of the particles; and
determining the physical characteristics from the heightmap representations.

6. The method of claim 5, wherein the physical characteristics comprise one or more of: particle size, particle shape, or particle sphericity.

7. The method of claim 5, wherein determining the physical characteristics comprises applying the heightmap representations of the particles to a dimension reducer to obtain the physical characteristics of the particles.

8. The method of claim 1, wherein generating the multispherical approximation comprises applying the physical characteristics of the set of particles to an autoencoder trained to output the multispherical approximations from input comprising the physical characteristics.

9. The method of claim 1, comprising determining the final recipe at least by iteratively altering the proposed recipe and predicting performance of the altered proposed recipe until the predicted performance satisfies performance criteria to obtain the final recipe.

10. The method of claim 9, wherein the performance criteria comprises a highest dry packing rating subject to an acceptable wet flowability rating.

11. The method of claim 1, comprising:
mixing a concrete mixture using the final recipe;
evaluating performance of the concrete mixture using one or more performance tests; and
updating the performance rules based on the evaluated performance of the concrete mixture.

12. The method of claim 11, wherein updating the performance rules comprises generating, based on the evaluated performance, a limit curve for sets of particles matching the physical characteristics of the set of particles.

13. The method of claim 11, wherein updating the performance rules comprises adjusting, based on the evaluated performance, a limit curve of a database of performance rules for sets of particles matching the physical characteristics of the set of particles.

14. The method of claim 1, wherein the performance rules include curves representing wet flowability limits.

15. The method of claim 1, comprising determining the dry packing rating by applying the multispherical approximation of the set of particles to a physics simulator.

16. The method of claim 1, wherein the sensor measurements comprise an optical characterization of the set of particles obtained by scanning the set of particles with an imaging device.

17. The method of claim 16, wherein the multispherical approximation has reduced dimensionality compared to the optical characterization.

18. The method of claim 1, wherein the physical characteristics have reduced dimensionality compared to the sensor measurements.

19. A system comprising one or more computers and one or more storage devices on which are stored instructions that are operable, when executed by the one or more computers, to cause the one or more computers to perform operations comprising:
determining, based on sensor measurements of a set of particles, physical characteristics of the set of particles;
generating, based on the physical characteristics, a multispherical approximation of the set of particles;
predicting performance of a proposed recipe for a concrete mixture formed from the set of particles to obtain a predicted performance by determining a wet flowability rating of the proposed recipe based on performance rules relevant to the physical characteristics of the set of particles, and determining a dry packing rating of the proposed recipe based on the multispherical approximation; and
outputting a final recipe based on the proposed recipe.

20. One or more non-transitory computer readable storage devices storing instructions that, when executed by at least one processor, cause the at least one processor to perform operations comprising:
determining, based on sensor measurements of a set of particles, physical characteristics of the set of particles;
generating, based on the physical characteristics, a multispherical approximation of the set of particles;
predicting performance of a proposed recipe for a concrete mixture formed from the set of particles to obtain a predicted performance by determining a wet flowability rating of the proposed recipe based on performance rules relevant to the physical characteristics of the set of particles, and determining a dry packing rating of the proposed recipe based on the multispherical approximation; and
outputting a final recipe based on the proposed recipe.

* * * * *